(12) United States Patent
Morgan et al.

(10) Patent No.: US 7,186,538 B2
(45) Date of Patent: Mar. 6, 2007

(54) **TYPE II RESTRICTION ENDONUCLEASE, CSTMI, OBTAINABLE FROM *CORYNEBACTERIUM STRIATUM* M82B AND A PROCESS FOR PRODUCING THE SAME**

(75) Inventors: Richard D. Morgan, Middleton, MA (US); Tanya Bhatia, Peabody, MA (US)

(73) Assignee: New England Biolabs, Inc., Ipswich, MA (US)

( * ) Notice: Subject to any disclaimer, the term of this patent is extended or adjusted under 35 U.S.C. 154(b) by 225 days.

(21) Appl. No.: 10/616,689

(22) Filed: Jul. 10, 2003

(65) Prior Publication Data

US 2005/0009034 A1   Jan. 13, 2005

(51) Int. Cl.
*C12N 9/22* (2006.01)
*C12N 15/55* (2006.01)

(52) U.S. Cl. ............... 435/199; 435/320.1; 435/252.3; 536/23.2

(58) Field of Classification Search .............. None
See application file for complete search history.

(56) References Cited

FOREIGN PATENT DOCUMENTS

WO   WO 2004/007670 A2   1/2004

OTHER PUBLICATIONS

Tauch, A., et al. (2000) Accession No. AF024666.*
Tauch, A., et al. (1998) Plasmid 40, 126-139.*
Endow, et al., J. Mol. Biol. 112:521 (1977).
Waalwijk, et al. Nucleic Acids Res. 5:3231 (1978).
Gingeras and Brooks, Proc. Natl. Acad. Sci. USA 80:402 (1983).
Tauch, et al., Mol. Gen. Genet. 263:1-11 (2000).
Skoglund, Gene 88:1-5 (1990).
Tucholski, et al. Gene 223:293-302 (1998).
Tucholski, et al., Gene 157:87-92 (1995).
Boyd, et al., Nucleic Acids Res. 14:5255-52744 (1986).

* cited by examiner

*Primary Examiner*—Charles L. Patterson, Jr.
(74) *Attorney, Agent, or Firm*—Harriet M. Strimpel

(57) ABSTRACT

In accordance with the present invention, there is provided a novel type II restriction endonuclease, obtainable from *Corynebacterium striatum* M82B, hereinafter referred to as "CstMI", which endonuclease:

(1) recognizes the nucleotide sequence 5'-AAGGAG-3' in a double-stranded DNA molecule as shown below,

```
5'-AAGGAGN20↓-3'

3'-TTCCTCN18↑-5'
```

(wherein G represents guanine, C represents cytosine, A represents adenine, T represents thymine and N represents either G, C, A, or T);

(2) cleaves said sequence at the phosphodiester bonds between the 20th and the 21st nucleotides 3' to the recognition sequence in the 5'-AAGGAG-3 strand of the DNA, and between the 18th and 19th nucleotides 5' to the recognition sequence in the complement stand, 5'-CTCCTT-3', to produce a 2 base 3'extension; and (3) possesses a second enzymatic activity that recognizes the same DNA sequence, 5'-AAGGAG-3', but modifies this sequence by the addition of a methyl group to prevent cleavage by the CstMI endonuclease activity.

6 Claims, 10 Drawing Sheets

CstMI Figure 1 - Agarose gel showing CstMI cleavage of lambda, T7, phiX174, pBR322 and pUC19 DNAs.
1  2  3  4  5  6   7  8  9  10 11 12 13 14 15 16 17 18 19 20
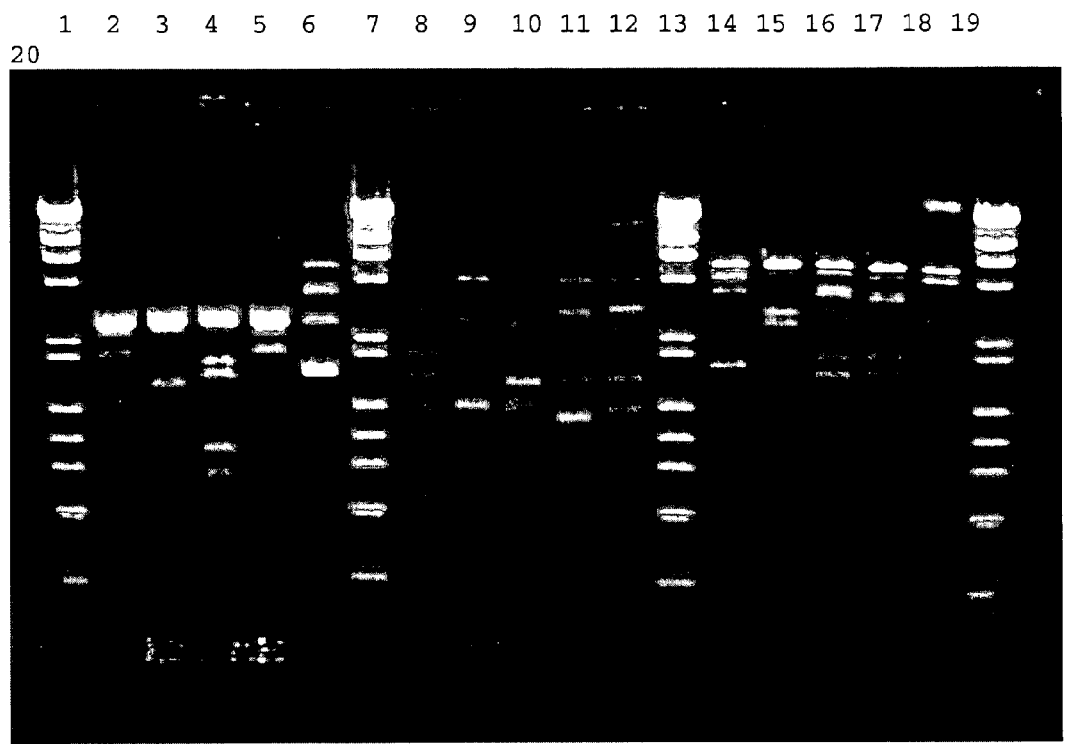

CstMI Figure 2 - DNA sequence of the CstMI gene locus (SEQ ID NO )

```
   1 ATGGTTATGG CCCCTACGAC TGTTTTTGAC CGCGCTACCA TTCGCCACAA
  51 TCTCACCGAA TTCAAACTCC GGTGGCTTGA CCGCATTAAG CAATGGGAGG
 101 CGGAAAACCG ACCCGCAACC GAGTCGAGTC ACGACCAACA GTTCTGGGGT
 151 GACCTGCTCG ACTGCTTCGG TGTCAACGCC CGCGACCTGT ACTTGTACCA
 201 ACGCAGCGCT AAACGCGCTT CGACGGGGCG CACCGGCAAG ATCGACATGT
 251 TTATGCCGGG CAAAGTCATA GGCGAGGCTA AGTCCCTCGG CGTCCCGCTC
 301 GATGATGCTT ATGCCCAAGC TTTGGATTAT TTGCTGGGCG GTACTATCGC
 351 GAACTCGCAC ATGCCGGCCT ATGTTGTCTG CTCCAACTTC GAGACCCTGC
 401 GGGTTACCCG TCTTAACCGC ACCTATGTCG GCGATAGCGC CGACTGGGAC
 451 ATTACATTCC CTTTAGCTGA GATTGACGAG CACATCGAAC AACTCGCTTT
 501 TCTCGCCGAC TATGAAACCT CCGCCTACCG GGAGGAAGAA AAGGCTTCCC
 551 TGGAAGCCTC TCGGTTAATG GTGGAGCTCT TCCGCGCCAT GAACGGCGAC
 601 GACGTGGACG AGGCAGTAGG CGATGACGCT CCCACCACGC CGGAGGAAGA
 651 AGACGAGCGC GTCATGCGCA CCTCTATCTA CCTCACCCGA ATCCTCTTCC
 701 TTCTCTTCGG CGACGACGCA GGACTCTGGG ATACCCCGCA TTTGTTTGCG
 751 GACTTTGTGC GCAATGAAAC CACCCCAGAA TCGCTCGGCC CGCAGCTCAA
 801 TGAGCTATTT AGCGTGCTTA ATACCGCCCG GGAAAAGCGG CCTAAGCGTT
 851 TGCCATCAAC GTTGGCGAAG TTTCCTTATG TCAATGGTGC CCTATTTGCT
 901 GAACCGTTGG CCTCGGAGTA CTTCGACTAC CAGATGCGCG AAGCATTGCT
 951 TGCTGCCTGC GACTTCGACT GGTCGACCAT TGACGTCTCC GTCTTTGGTT
1001 CGTTGTTCCA ATTGGTGAAA TCGAAGGAAG CGCGCCGCAG CGACGGCGAA
1051 CACTACACGT CTAAGGCCAA CATCATGAAG ACCATCGGCC CGCTGTTTTT
1101 GGACGAGCTG AGGGCTGAGG CCGATAAGTT GGTGTCTTCT CCGTCGACGT
1151 CGGTGGCCGC ATTAGAGCGC TTCCGCGACT CCCTGTCTGA GCTGGTATTC
1201 GCTGATATGG CTTGTGGTTC TGGAAACTTC CTGCTTCTGG CGTATCGGGA
1251 GTTGCGCCGG ATTGAAACCG ACATCATTGT CGCTATACGC CAGCGCCGCG
1301 GTGAAACGGG CATGTCGTTG AATATTGAGT GGGAGCAGAA ACTGTCCATT
1351 GGGCAGTTCT ACGGCATTGA GCTGAATTGG TGGCCTGCCA AGATTGCTGA
1401 GACTGCCATG TTCCTAGTTG ACCATCAGGC CAACAAGGAG CTTGCCAACG
1451 CTGTGGGTAG GCCTCCGGAG CGGTTGCCGA TTAAGATTAC CGCGCACATT
1501 GTGCACGGCA ATGCCCTGCA GCTTGATTGG GCAGACATAC TCTCGGCTTC
```

FIG. 2 (cont'd)

```
1551  TGCCGCCAAG ACGTATATCT TCGGTAACCC GCCGTTTTTG GGGCATGCGA
1601  CGAGAACTGC TGAACAAGCT CAAGAACTCC GAGACTTGTG GGGCACTAAG
1651  GACATTTCAC GCTTGGACTA CGTCACCGGC TGGCATGCAA AGTGCTTGGA
1701  TTTCTTTAAG TCCCGAGAGG GTCGTTTTGC GTTTGTCACC ACCAATTCAA
1751  TTACTCAAGG TGATCAAGTT CCACGGCTAT TTGGGCCTAT CTTCAAAGCA
1801  GGGTGGCGTA TTCGTTTCGC TCACCGCACG TTTGCGTGGG ACTCTGAAGC
1851  ACCCGGTAAA GCTGCTGTTC ACTGCGTCAT TGTTGGCTTC GATAAGGAGA
1901  GTCAACCACG TCCACGTCTG TGGGATTATC CCGATGTAAA GGGCGAGCCA
1951  GTCTCAGTGG AAGTAGGCCA GTCCATTAAT GCCTATTTAG TAGACGGCCC
2001  TAATGTTCTT GTCGATAAAT CCCGGCATCC TATTTCGTCG GAAATATCGC
2051  CCGCAACTTT TGGAAATATG GCGCGAGATG GCGGCAACCT TCTAGTTGAG
2101  GTCGACGAAT ACGACGAGGT TATGAGTGAC CCCGTAGCGG CAAAGTATGT
2151  TCGCCCTTTC CGGGGTAGTC GAGAGCTAAT GAACGGCTTA GATCGGTGGT
2201  GTCTATGGCT TGTAGATGTA GCACCGTCAG ACATTGCCCA GAGTCCGGTT
2251  CTGAAAAAGC GTCTAGAAGC GGTTAAGTCT TTTCGAGCCG ACAGTAAAGC
2301  GGCAAGTACA CGGAAAATGG CTGAAACTCC GCACTTATTC GGCCAGCGGT
2351  CGCAACCGGA TACTGATTAC CTTTGCCTGC CGAAGGTAGT AAGCGAACGC
2401  CGCTCGTATT TCACCGTACA AAGGTATCCA TCAAACGTAA TCGCTTCTGA
2451  CCTAGTATTC CATGCTCAAG ATCCAGACGG CCTGATGTTT GCGCTAGCGT
2501  CGTCGTCGAT GTTCATTACG TGGCAGAAAA GCATCGGAGG ACGACTCAAG
2551  TCTGATCTCC GTTTTGCTAA CACTTTGACG TGGAATACTT TCCCAGTGCC
2601  AGAACTCGAC GAGAAGACGC GGCAGCGAAT TATTAAAGCG GGCAAGAAGG
2651  TGCTCGACGC CCGCGCGCTG CACCCAGAAC GCTCGCTGGC CGAGCACTAC
2701  AACCCACTCG CGATGGCACC GGAACTCATC AAAGCGCATG ATGCGCTCGA
2751  CCGCGAGGTG GATAAAGCGT TGGCGCGCC ACGAAAGCTG ACAACTGTTC
2801  GGCAGCGCCA GGAGCTATTG TTTGCCAATT ACGAAAAACT CATCTCACAC
2851  CAGCCCTAG
```

CstMI Figure 3: Amino acid sequence of the CstMI gene locus (SEQ ID NO:).

```
  1  MVMAPTTVFD RATIRHNLTE FKLRWLDRIK QWEAENRPAT ESSHDQQFWG
 51  DLLDCFGVNA RDLYLYQRSA KRASTGRTGK IDMFMPGKVI GEAKSLGVPL
101  DDAYAQALDY LLGGTIANSH MPAYVVCSNF ETLRVTRLNR TYVGDSADWD
151  ITFPLAEIDE HIEQLAFLAD YETSAYREEE KASLEASRLM VELFRAMNGD
201  DVDEAVGDDA PTTPEEEDER VMRTSIYLTR ILFLLFGDDA GLWDTPHLFA
251  DFVRNETTPE SLGPQLNELF SVLNTAPEKR PKRLPSTLAK FPYVNGALFA
301  EPLASEYFDY QMREALLAAC DFDWSTIDVS VFGSLFQLVK SKEARRSDGE
351  HYTSKANIMK TIGPLFLDEL RAEADKLVSS PSTSVAALER FRDSLSELVF
401  ADMACGSGNF LLLAYRELRR IETDIIVAIR QRRGETGMSL NIEWEQKLSI
451  GQFYGIELNW WPAKIAETAM FLVDHQANKE LANAVGRPPE RLPIKITAHI
501  VHGNALQLDW ADILSASAAK TYIFGNPPFL GHATRTAEQA QELRDLWGTK
551  DISRLDYVTG WHAKCLDFFK SREGRFAFVT TNSITQGDQV PRLFGPIFKA
601  GWRIRFAHRT FAWDSEAPGK AAVHCVIVGF DKESQPRPRL WDYPDVKGEP
651  VSVEVGQSIN AYLVDGPNVL VDKSRHPISS EISPATFGNM ARDGGNLLVE
701  VDEYDEVMSD PVAAKYVRPF RGSRELMNGL DRWCLWLVDV APSDIAQSPV
751  LKKRLEAVKS FRADSKAAST RKMAETPHLF GQRSQPDTDY LCLPKVVSER
801  RSYFTVQRYP SNVIASDLVF HAQDPDGLMF ALASSSMFIT WQKSIGGRLK
851  SDLRFANTLT WNTFPVPELD EKTRQRIIKA GKKVLDARAL HPERSLAEHY
901  NPLAMAPELI KAHDALDREV DKAFGAPRKL TTVRQRQELL FANYEKLISH
951  QP
```

Figure 4 - Agarose gel showing CstMI protection of pTBCstMI.3 DNA and cleavage of unmodified DNA substrate.
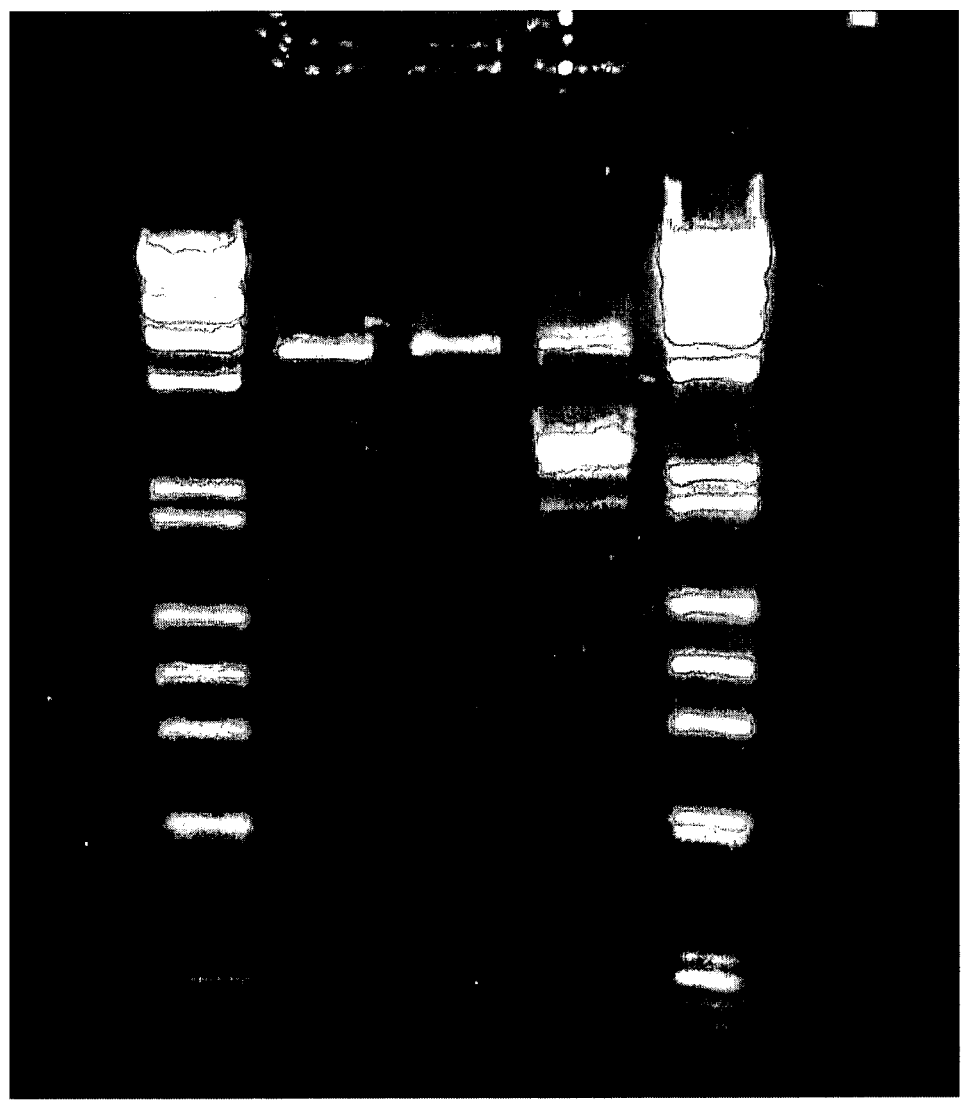

CstMI Figure 5 : Determination of the CstMI cleavage site.

Figure 5A: Location of cleavage on 5'-AAGGAG-3' strand.

pUC19-Adeno2BC4 DNA was cut with CstMI producing ends as indicated by the arrows:
5'-..CGAACCCAGGTGTGCGACG↓TCAGACAACGGGGGAGCGCTCCTTTTG..-3'
(SEQ ID NO:3)
3'-..GCTTGGGTCCACACGCT↑GCAGTCTGTTGCCCCCTCGCGAGGAAAAC..-5'

The resulting cleaved DNA:
5'-..CGAACCCAGGTGTGCGACG-3' (SEQ ID NO:4)
3'-..GCTTGGGTCCACACGCT-5'

The template strand for dideoxy DNA sequencing extension:
3'-..GGGTCCACACGCT-5'

The primer (NEB1224) is annealed and extended through the CstMI site. When the reaction reaches the end of the molecule the Taq polymerase adds an extra A base.

5'-PRIMER->. . CGAACCCAGGTGTGCGA(A)-3' (SEQ ID NO:5)
3'-. . . . . . GCTTGGGTCCACACGCT-(N20-GAGGAA)-5'

Sequencing Profile of CstMI cut pUC19-Adeno2BC4 DNA (ABI377 Sequencer)

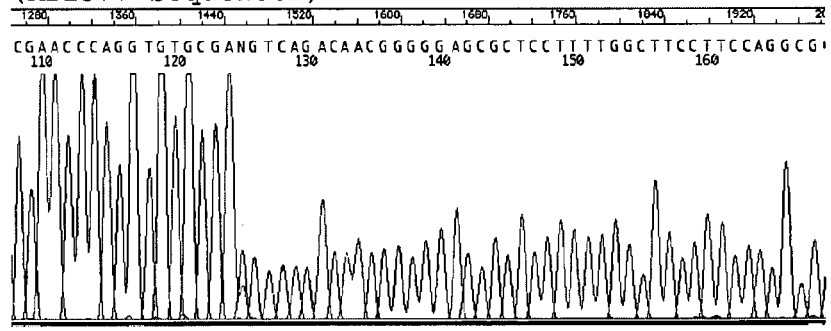

CstMI Figure 5: Determination of the CstMI cleavage site.

Figure 5B: Location of cleavage on 5'-CTCCTT-3' strand.

pBR322 DNA was cut with CstMI, yielding ends indicated by the arrows:

5'-..TGCATGCAAGGAGATGGCGCCCAACAGTCCCCC↓GGCCACGGGGCC..-3'
    (SEQ ID NO:6)
3'-..ACGTACGTTCCTCTACCGCGGGTTGTCAGGG↑GGCCGGTGCCCCGG..-5'

The resulting cleaved DNA:
5'-..TGCATGCAAGGAGATGGCGCCCAACAGTCCCCC -3'
    (SEQ ID NO:7)
3'-..ACGTACGTTCCTCTACCGCGGGTTGTCAGGG -5'

The template strand for dideoxy DNA sequencing extension:
3'-..ACGTACGTTCCTCTACCGCGGGTTGTCAGGG -5'

The primer (NEB1242) is annealed and extended through the CstMI site. When the reaction reaches the end of the molecule the Taq polymerase adds an extra A base.

5'-PRIMER->. TGCATGCAAGGAGATGGCGCCCAACAGTCCC(A)-3'
    (SEQ ID NO:8)
3'-. . . . . ACGTACGTTCCTCTACCGCGGGTTGTCAGGG -5'

Sequencing Profile of CstMI pBR322 DNA (ABI377 Sequencer)

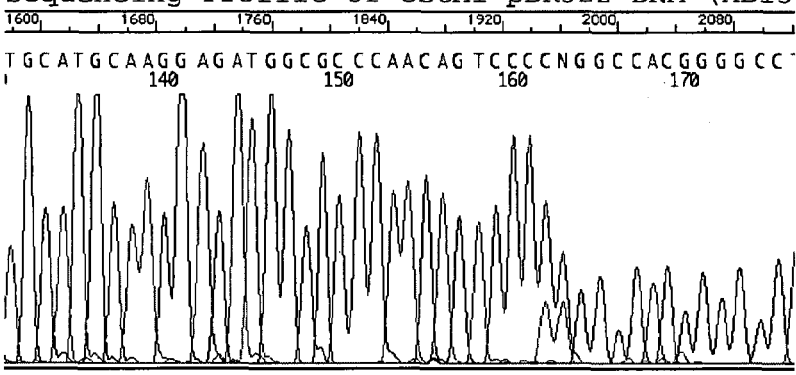

CstMI Figure 6: Sequence alignment of CstMI and MmeI amino acid sequences.

Symbol comparison table: /gcg/bin/gcgcore/data/rundata/blosum62.cmp
CompCheck: 1102

```
        Gap Weight:       8    Average Match:    2.778
     Length Weight:       2    Average Mismatch: -2.248

Quality:    1548           Length:      942
             Ratio:    1.718            Gaps:       19
Percent Similarity:   51.009   Percent Identity:  39.574

Match display thresholds for the alignment(s):
                     | = IDENTITY
                     : = 2
                     . = 1
```

CstMI.pep x MmeI.pep    June 20, 2003 11:45

```
 20 EFKLRWLDRIKQWEAENRPATESSHDQQFWGDLLDCFGVNARDLYLYQRS  69
    | : : :: |.||    .|.|  .| |  : ||:  : .  ::..
  7 EIRRKAIEFSKRWE...DASDENSQAKPFLIDFFEVFGITNKRVATFEHA  53

70 AKRASTGR....TGKIDMFMPGKVIGEAKSLGVPLDDAYAQALDYLLGGT 115
    |: .         | :|:| ||  .: | ||| || || |||||   |
 54 VKKFAKAHKEQSRGFVDLFWPGILLIEMKSRGKDLDKAYDQALDYFSG.. 101

116 IANSHMPAYVVCSNFETLRVTRLNRTYVGDSADWDITFPLAEIDEHIEQL 165
    ||  :| ||. .|: |.| |          :|    : || :: :.:
102 IAERDLPRYVLVCDFQRFRLTDL...ITKES....VEFLLKDLYQNVRSF 144

166 AFLADYETSAYREEEKASLEASRLMVELFRAMNGDDVDEAVGDDAPTTPE 215
    |:| |:|   :  :: ..-|. |.|      |  .|| :
145 GFIAGYQTQVIKPQDPINIKAAERMGKL......HDTLKLVGYEGHA... 185

216 EEDERVMRTSIYLTRILFLLFGDDAGLWDTPHLFADFVRNETTPE..SLG 263
                   :|| |:|| || :|  :.:   || :::  .|  :   |
186 ........LELYLVRLLFCLPAEDTTIFE.KSLFQEYIETKTLEDGSDLA 236

264 PQLNELFSVLNTAPEKRPKRLPSTLAKPFYVNGALFAEPLASEYFDYQMR 313
    :| || ||||  :|  | |      || |||:||  || |||    || ||
227 MHINTLFYVLNTPEQKRLKNLDEHLAAFPYINGKLFEEPLPPAQFDKAMR 276

314 EALLAACDFDWSTIDVSVFGSLFQLVKSKEARHSDGEHYTSKANIMKTIG 363
    ||||   |   ||| |   .:|||||| :   . ||. | ||||.|||:| |
277 EALLDLCSLDWSRISPAIFGSLFQSIMDAKKRHNLGAHYTSEANILKLIK 326

364 PLFLDELRAEADKLVSSPSTSVAALERFRDSLSELVFADMACGSGNFLLL 413
    ||||||| |  :|. ... .|    |   | | | | | ||| ||||.:
327 PLFLDELWVEFEKVKNMKNKLLA....FHKKLRGLTFFDPACGCGNFLVI 372

414 AYRELRRIETDIIVAIRQRRGETGMSLNIEWEQKLSIGQFYGIELWWWPA 463
    |||||  :|  ::: :    ||:    |.||     .:.:  ||:|||:   .||
373 TYRELRLLEIEVLRGL.HRGGQ..QVLDIEHLIQINVDQFPGIEIEEFPA 419

464 KIAETAMFLVDHQANKELANAVGRPPERLPIKITAHIVHGNALQLDWADI 513
    .||:  |:.| ||| |  .:..    |   |:|:|  | ||..  ||||:|| |:
420 QIAQVALWLTDHQMNMKISDEPGNYFARIPLKSTPHILNANALQIDWNDV 469

514 LSASAAKTYIFGNPPFLGHATRTAEQAQELRDLWGT.KDISRLDYVTGWH 562
    | |        :|  |||||.|  . .|   |   :|   ..|   | | |||  |:
```

FIG. 6 (cont'd)

```
470 LEAKKC.CFILGNPPFVGKSKQTPGQKADLLSVFGNLKSASDLDLVAAWY 518

563 AKCLDFFKSREG.RFAFVTTNSITQGDQVPRLFGPIFKAGWRIRFAHRTF 611
    |  : ..   | |||.|||||||:||  |.  :    | :| ||||||
519 PKAAHYIQTNANIRCAFVSTNSITQGEQVSLLWPLLLSLGIKINFAHRTF 568

612 AWDSEAPGKAAVHCVIVGFDKESQPRPRLWDYPDVKGEFVSVEVGQSINA 661
    .|  .|| |  ||||||||:||  .      :::|   : |||..:.  ..||
569 SWTNEASGVAAVHCVIIGPGLKDSDEKIIYEYESINGEPLAIK.AKNINP 617

662 YLVDGPNVLVDKSRHPISSEISPATFGNMARDGGNLLVEVDEYDE.VMSD 710
    || || .|:  | . || |.:     :||  | ||| |  :| .: .  .:
618 YLRDGVDVIACKRQQPI.SKLPSMRYGNKPTDDGNFLFTDEEKNQFITNE 666

711 FVAAKYVRPFRGSRELMNGLDRWCLWLVDVAPSDIAQSPVLKKRLEAVKS 760
    |  .|| | |  |  .| ||||||   |:|   |.. |:.  |.
667 PSSEKYFRRFVGGDEFINNTSRWCLWLDGADISEIRAMPLVLARIKKVQE 716

761 FRADSKAASTRKMAETPHLFGQRSQPDTDYLCLPKVVSERRSYFTVQRYP 810
    ||  ||  ||.| ||  |    |||||||| :|.  || | :    :
717 FRLKSSAKPTRQSASTPMKFFYISQPDTDYLLIPETSSENRQFIPIGFVD 766

811 SNVIASDLVFHAQDPDGLMFALASSSMPITWQKSIGGRLKSDLRFANTLT 860
    |||.|.  :|   : |-|  | ||.|   | :.:||||.|  |:.  .|
767 RNVISSNATYHIPSAEPLIFGLLSSTMHNCWMRNVGGRLESRYRYSASLV 816

861 WNTFPVPELDEKTRQRIIKAGKKVLDARALHPERSLAEHYNPLAMAPELI 910
    :||||  : .||  . |  .|   :| ||.  :|  |||  |.|   | ||:
817 YNTPPWIQPNEKQSKAIEEAAFAILKARSNYPHESLAGLYDPKTMPSELL 866

911 KAHDALDREVDKAFGAPRKLTTVRQRQELLFANYEKLISHQP 952
    |||  ||:  ||   :|     | :   |   ||  |:|:   |  |
867 KAHQKLDKAVDSVYGPKGPNTEI.ARIAFLFETYQKMTSLLP 907
```

SEQUENCE LISTING

<160> NUMBER OF SEQ ID NOS: 17

<210> SEQ ID NO 1
<211> LENGTH: 2859
<212> TYPE: DNA
<213> ORGANISM: CstMI gene locus

<400> SEQUENCE: 1

| | | | | | |
|---|---|---|---|---|---|
| atggttatgg | cccctacgac | tgtttttgac | cgcgctacca | ttcgccacaa | tctcaccgaa | 60 |
| ttcaaactcc | ggtggcttga | ccgcattaag | caatgggagg | cggaaaaccg | acccgcaacc | 120 |
| gagtcgagtc | acgaccaaca | gttctggggt | gacctgctcg | actgcttcgg | tgtcaacgcc | 180 |
| cgcgacctgt | acttgtacca | acgcagcgct | aaacgcgctt | cgacggggcg | caccggcaag | 240 |
| atcgacatgt | ttatgccggg | caaagtcata | ggcgaggcta | agtccctcgg | cgtcccgctc | 300 |
| gatgatgctt | atgcccaagc | tttgattat | ttgctgggcg | gtactatcgc | gaactcgcac | 360 |
| atgccggcct | atgttgtctg | ctccaacttc | gagaccctgc | gggttacccg | tcttaaccgc | 420 |
| acctatgtcg | gcgatagcgc | cgactgggac | attacattcc | ctttagctga | gattgacgag | 480 |
| cacatcgaac | aactcgcttt | tctcgccgac | tatgaaacct | ccgcctaccg | ggaggaagaa | 540 |
| aaggcttccc | tggaagcctc | tcggttaatg | gtggagctct | ccgcgccat | gaacggcgac | 600 |
| gacgtggacg | aggcagtagg | cgatgacgct | cccaccacgc | cggaggaaga | agacgagcgc | 660 |
| gtcatgcgca | cctctatcta | cctcacccga | atcctcttcc | ttctcttcgg | cgacgacgca | 720 |
| ggactctggg | ataccccgca | tttgtttgcg | gactttgtgc | gcaatgaaac | caccccagaa | 780 |
| tcgctcggcc | cgcagctcaa | tgagctattt | agcgtgctta | ataccgcccc | ggaaaagcgg | 840 |
| cctaagcgtt | tgccatcaac | gttggcgaag | tttccttatg | tcaatggtgc | cctatttgct | 900 |
| gaaccgttgg | cctcggagta | cttcgactac | cagatgcgcg | aagcattgct | tgctgcctgc | 960 |
| gacttcgact | ggtcgaccat | tgacgtctcc | gtctttggtt | cgttgttcca | attggtgaaa | 1020 |
| tcgaaggaag | cgcgccgcag | cgacggcgaa | cactacacgt | ctaaggccaa | catcatgaag | 1080 |
| accatcggcc | cgctgttttt | ggacgagctg | agggctgagg | ccgataagtt | ggtgtcttct | 1140 |
| ccgtcgacgt | cggtggccgc | attagagcgc | ttccgcgact | ccctgtctga | gctggtattc | 1200 |
| gctgatatgg | cttgtggttc | tggaaacttc | ctgcttctgg | cgtatcggga | gttgcgccgg | 1260 |
| attgaaaccg | acatcattgt | cgctatacgc | cagcgccgcg | gtgaaacggg | catgtcgttg | 1320 |
| aatattgagt | gggagcagaa | actgtccatt | gggcagttct | acggcattga | gctgaattgg | 1380 |
| tggcctgcca | agattgctga | gactgccatg | ttcctagttg | accatcaggc | caacaaggag | 1440 |
| cttgccaacg | ctgtgggtag | gcctccggag | cggttgccga | ttaagattac | cgcgcacatt | 1500 |
| gtgcacggca | atgccctgca | gcttgattgg | gcagacatac | tctcggcttc | tgccgccaag | 1560 |
| acgtatatct | tcggtaaccc | gccgttttg | gggcatgcga | cgagaactgc | tgaacaagct | 1620 |
| caagaactcc | gagacttgtg | gggcactaag | gacatttcac | gcttggacta | cgtcaccggc | 1680 |
| tggcatgcaa | agtgcttgga | tttctttaag | tcccgagagg | gtcgttttgc | gtttgtcacc | 1740 |
| accaattcaa | ttactcaagg | tgatcaagtt | ccacggctat | ttgggcctat | cttcaaagca | 1800 |
| gggtggcgta | ttcgtttcgc | tcaccgcacg | tttgcgtggg | actctgaagc | acccggtaaa | 1860 |
| gctgctgttc | actgcgtcat | tgttggcttc | gataaggaga | gtcaaccacg | tccacgtctg | 1920 |
| tgggattatc | ccgatgtaaa | gggcgagcca | gtctcagtgg | aagtaggcca | gtccattaat | 1980 |
| gcctatttag | tagacggccc | taatgttctt | gtcgataaat | cccggcatcc | tatttcgtcg | 2040 |

-continued

```
gaaatatcgc cgcaactttt tggaaatatg gcgcgagatg gcggcaacct tctagttgag    2100
gtcgacgaat acgacgaggt tatgagtgac cccgtagcgg caaagtatgt tcgcccttc    2160 cggggtagtc gagagctaat gaacggctta gatcggtggt gtctatggct tgtagatgta    2220
gcaccgtcag acattgccca gagtccggtt ctgaaaaagc gtctagaagc ggttaagtct    2280
tttcgagccg acagtaaagc ggcaagtaca cggaaaatgg ctgaaactcc gcacttattc    2340
ggccagcggt cgcaaccgga tactgattac ctttgcctgc cgaaggtagt aagcgaacgc    2400
cgctcgtatt tcaccgtaca aaggtatcca tcaaacgtaa tcgcttctga cctagtattc    2460
catgctcaag atccagacgg cctgatgttt gcgctagcgt cgtcgtcgat gttcattacg    2520
tggcagaaaa gcatcggagg acgactcaag tctgatctcc gttttgctaa cactttgacg    2580
tggaatactt tcccagtgcc agaactcgac gagaagacgc ggcagcgaat tattaaagcg    2640
ggcaagaagg tgctcgacgc ccgcgcgctg cacccagaac gctcgctggc cgagcactac    2700
aacccactcg cgatggcacc ggaactcatc aaagcgcatg atgcgctcga ccgcgaggtg    2760
gataaagcgt ttggcgcgcc acgaaagctg acaactgttc ggcagcgcca ggagctattg    2820
tttgccaatt acgaaaaact catctcacac cagccctag                           2859
```

<210> SEQ ID NO 2
<211> LENGTH: 952
<212> TYPE: PRT
<213> ORGANISM: CstMi gene locus

<400> SEQUENCE: 2

```
Met Val Met Ala Pro Thr Thr Val Phe Asp Arg Ala Thr Ile Arg His
1               5                   10                  15

Asn Leu Thr Glu Phe Lys Leu Arg Trp Leu Asp Arg Ile Lys Gln Trp
            20                  25                  30

Glu Ala Glu Asn Arg Pro Ala Thr Glu Ser Ser His Asp Gln Gln Phe
        35                  40                  45

Trp Gly Asp Leu Leu Asp Cys Phe Gly Val Asn Ala Arg Asp Leu Tyr
    50                  55                  60

Leu Tyr Gln Arg Ser Ala Lys Arg Ala Ser Thr Gly Arg Thr Gly Lys
65                  70                  75                  80

Ile Asp Met Phe Met Pro Gly Lys Val Ile Gly Glu Ala Lys Ser Leu
                85                  90                  95

Gly Val Pro Leu Asp Asp Ala Tyr Ala Gln Ala Leu Asp Tyr Leu Leu
            100                 105                 110

Gly Gly Thr Ile Ala Asn Ser His Met Pro Ala Tyr Val Val Cys Ser
        115                 120                 125

Asn Phe Glu Thr Leu Arg Val Thr Arg Leu Asn Arg Thr Tyr Val Gly
    130                 135                 140

Asp Ser Ala Asp Trp Asp Ile Thr Phe Pro Leu Ala Glu Ile Asp Glu
145                 150                 155                 160

His Ile Glu Gln Leu Ala Phe Leu Ala Asp Tyr Glu Thr Ser Ala Tyr
                165                 170                 175

Arg Glu Glu Glu Lys Ala Ser Leu Glu Ala Ser Arg Leu Met Val Glu
            180                 185                 190

Leu Phe Arg Ala Met Asn Gly Asp Asp Val Asp Glu Ala Val Gly Asp
        195                 200                 205

Asp Ala Pro Thr Thr Pro Glu Glu Glu Asp Glu Arg Val Met Arg Thr
    210                 215                 220
```

```
Ser Ile Tyr Leu Thr Arg Ile Leu Phe Leu Leu Phe Gly Asp Asp Ala
225                 230                 235                 240

Gly Leu Trp Asp Thr Pro His Leu Phe Ala Asp Phe Val Arg Asn Glu
            245                 250                 255

Thr Thr Pro Glu Ser Leu Gly Pro Gln Leu Asn Glu Leu Phe Ser Val
        260                 265                 270

Leu Asn Thr Ala Pro Glu Lys Arg Pro Lys Arg Leu Pro Ser Thr Leu
    275                 280                 285

Ala Lys Phe Pro Tyr Val Asn Gly Ala Leu Phe Ala Glu Pro Leu Ala
    290                 295                 300

Ser Glu Tyr Phe Asp Tyr Gln Met Arg Glu Ala Leu Leu Ala Ala Cys
305                 310                 315                 320

Asp Phe Asp Trp Ser Thr Ile Asp Val Ser Val Phe Gly Ser Leu Phe
            325                 330                 335

Gln Leu Val Lys Ser Lys Glu Ala Arg Arg Ser Asp Gly Glu His Tyr
            340                 345                 350

Thr Ser Lys Ala Asn Ile Met Lys Thr Ile Gly Pro Leu Phe Leu Asp
    355                 360                 365

Glu Leu Arg Ala Glu Ala Asp Lys Leu Val Ser Pro Ser Thr Ser
370                 375                 380

Val Ala Ala Leu Glu Arg Phe Arg Asp Ser Leu Ser Glu Leu Val Phe
385                 390                 395                 400

Ala Asp Met Ala Cys Gly Ser Gly Asn Phe Leu Leu Leu Ala Tyr Arg
            405                 410                 415

Glu Leu Arg Arg Ile Glu Thr Asp Ile Ile Val Ala Ile Arg Gln Arg
            420                 425                 430

Arg Gly Glu Thr Gly Met Ser Leu Asn Ile Glu Trp Glu Gln Lys Leu
        435                 440                 445

Ser Ile Gly Gln Phe Tyr Gly Ile Glu Leu Asn Trp Trp Pro Ala Lys
    450                 455                 460

Ile Ala Glu Thr Ala Met Phe Leu Val Asp His Gln Ala Asn Lys Glu
465                 470                 475                 480

Leu Ala Asn Ala Val Gly Arg Pro Pro Glu Arg Leu Pro Ile Lys Ile
            485                 490                 495

Thr Ala His Ile Val His Gly Asn Ala Leu Gln Leu Asp Trp Ala Asp
            500                 505                 510

Ile Leu Ser Ala Ser Ala Ala Lys Thr Tyr Ile Phe Gly Asn Pro Pro
    515                 520                 525

Phe Leu Gly His Ala Thr Arg Thr Ala Glu Gln Ala Gln Glu Leu Arg
    530                 535                 540

Asp Leu Trp Gly Thr Lys Asp Ile Ser Arg Leu Asp Tyr Val Thr Gly
545                 550                 555                 560

Trp His Ala Lys Cys Leu Asp Phe Phe Lys Ser Arg Glu Gly Arg Phe
            565                 570                 575

Ala Phe Val Thr Thr Asn Ser Ile Thr Gln Gly Asp Gln Val Pro Arg
            580                 585                 590

Leu Phe Gly Pro Ile Phe Lys Ala Gly Trp Arg Ile Arg Phe Ala His
    595                 600                 605

Arg Thr Phe Ala Trp Asp Ser Glu Ala Pro Gly Lys Ala Ala Val His
    610                 615                 620

Cys Val Ile Val Gly Phe Asp Lys Glu Ser Gln Pro Arg Pro Arg Leu
625                 630                 635                 640

Trp Asp Tyr Pro Asp Val Lys Gly Glu Pro Val Ser Val Glu Val Gly
```

Gln Ser Ile Asn Ala Tyr Leu Val Asp Gly Pro Asn Val Leu Val Asp
                645                 650                 655

Lys Ser Arg His Pro Ile Ser Ser Glu Ile Ser Pro Ala Thr Phe Gly
    660                 665                 670

Asn Met Ala Arg Asp Gly Gly Asn Leu Leu Val Glu Val Asp Glu Tyr
675                 680                 685

Asp Glu Val Met Ser Asp Pro Val Ala Ala Lys Tyr Val Arg Pro Phe
        690                 695                 700

Arg Gly Ser Arg Glu Leu Met Asn Gly Leu Asp Arg Trp Cys Leu Trp
705                 710                 715                 720

Leu Val Asp Val Ala Pro Ser Asp Ile Ala Gln Ser Pro Val Leu Lys
            725                 730                 735

Lys Arg Leu Glu Ala Val Lys Ser Phe Arg Ala Asp Ser Lys Ala Ala
                740                 745                 750

Ser Thr Arg Lys Met Ala Glu Thr Pro His Leu Phe Gly Gln Arg Ser
    755                 760                 765

Gln Pro Asp Thr Asp Tyr Leu Cys Leu Pro Lys Val Val Ser Glu Arg
770                 775                 780

Arg Ser Tyr Phe Thr Val Gln Arg Tyr Pro Ser Asn Val Ile Ala Ser
785                 790                 795                 800

Asp Leu Val Phe His Ala Gln Asp Pro Asp Gly Leu Met Phe Ala Leu
            805                 810                 815

Ala Ser Ser Met Phe Ile Thr Trp Gln Lys Ser Ile Gly Gly Arg
                820                 825                 830

Leu Lys Ser Asp Leu Arg Phe Ala Asn Thr Leu Thr Trp Asn Thr Phe
    835                 840                 845

Pro Val Pro Glu Leu Asp Glu Lys Thr Arg Gln Arg Ile Ile Lys Ala
850                 855                 860

Gly Lys Lys Val Leu Asp Ala Arg Ala Leu His Pro Glu Arg Ser Leu
865                 870                 875                 880

Ala Glu His Tyr Asn Pro Leu Ala Met Ala Pro Glu Leu Ile Lys Ala
            885                 890                 895

His Asp Ala Leu Asp Arg Glu Val Asp Lys Ala Phe Gly Ala Pro Arg
                900                 905                 910

Lys Leu Thr Thr Val Arg Gln Arg Gln Glu Leu Leu Phe Ala Asn Tyr
    915                 920                 925

Glu Lys Leu Ile Ser His Gln Pro
930                 935                 940

945                 950

<210> SEQ ID NO 3
<211> LENGTH: 46
<212> TYPE: DNA
<213> ORGANISM: Unknown
<220> FEATURE:
<223> OTHER INFORMATION: pUC19-Adeno2BC4 DNA

<400> SEQUENCE: 3
cgaacccagg tgtgcgacgt cagacaacgg gggagcgctc cttttg                46

<210> SEQ ID NO 4
<211> LENGTH: 19
<212> TYPE: DNA
<213> ORGANISM: UNKNOWN
<220> FEATURE:
<223> OTHER INFORMATION: resulting cleaved DNA -continued

```
<400> SEQUENCE: 4
cgaacccagg tgtgcgacg                                                19

<210> SEQ ID NO 5
<211> LENGTH: 18
<212> TYPE: DNA
<213> ORGANISM: unknown
<220> FEATURE:
<223> OTHER INFORMATION: primer (NEB1224) (New England Biolabs, Inc.)

<400> SEQUENCE: 5
cgaacccagg tgtgcgaa                                                 18

<210> SEQ ID NO 6
<211> LENGTH: 45
<212> TYPE: DNA
<213> ORGANISM: unknown
<220> FEATURE:
<223> OTHER INFORMATION: pBR322 DNA cut with CstMI

<400> SEQUENCE: 6
tgcatgcaag gagatggcgc ccaacagtcc cccggccacg gggcc                   45

<210> SEQ ID NO 7
<211> LENGTH: 33
<212> TYPE: DNA
<213> ORGANISM: unknown
<220> FEATURE:
<223> OTHER INFORMATION: resulting cleaved DNA

<400> SEQUENCE: 7
tgcatgcaag gagatggcgc ccaacagtcc ccc                                33

<210> SEQ ID NO 8
<211> LENGTH: 32
<212> TYPE: DNA
<213> ORGANISM: unknown
<220> FEATURE:
<223> OTHER INFORMATION: primer (NEB1242)(New England Biolabs)

<400> SEQUENCE: 8
tgcatgcaag gagatggcgc ccaacagtcc ca                                 32

<210> SEQ ID NO 9
<211> LENGTH: 933
<212> TYPE: PRT
<213> ORGANISM: unknown
<220> FEATURE:
<223> OTHER INFORMATION: CstMI amino acid sequence

<400> SEQUENCE: 9

Glu Phe Lys Leu Arg Trp Leu Asp Arg Ile Lys Gln Trp Glu Ala Glu
1               5                   10                  15

Asn Arg Pro Ala Thr Glu Ser Ser His Asp Gln Gln Phe Trp Gly Asp
            20                  25                  30

Leu Leu Asp Cys Phe Gly Val Asn Ala Arg Asp Leu Tyr Leu Tyr Gln
        35                  40                  45

Arg Ser Ala Lys Arg Ala Ser Thr Gly Arg Thr Gly Lys Ile Asp Met
    50                  55                  60

Phe Met Pro Gly Lys Val Ile Gly Glu Ala Lys Ser Leu Gly Val Pro
65                  70                  75                  80

Leu Asp Asp Ala Tyr Ala Gln Ala Leu Asp Tyr Leu Leu Gly Gly Thr
                85                  90                  95
```

```
Ile Ala Asn Ser His Met Pro Ala Tyr Val Cys Ser Asn Phe Glu
            100                 105                 110

Thr Leu Arg Val Thr Arg Leu Asn Arg Thr Tyr Val Gly Asp Ser Ala
        115                 120                 125

Asp Trp Asp Ile Thr Phe Pro Leu Ala Glu Ile Asp Glu His Ile Glu
    130                 135                 140

Gln Leu Ala Phe Leu Ala Asp Tyr Glu Thr Ser Ala Tyr Arg Glu Glu
145                 150                 155                 160

Glu Lys Ala Ser Leu Glu Ala Ser Arg Leu Met Val Glu Leu Phe Arg
                165                 170                 175

Ala Met Asn Gly Asp Asp Val Asp Glu Ala Val Gly Asp Asp Ala Pro
            180                 185                 190

Thr Thr Pro Glu Glu Asp Glu Arg Val Met Arg Thr Ser Ile Tyr
        195                 200                 205

Leu Thr Arg Ile Leu Phe Leu Leu Phe Gly Asp Asp Ala Gly Leu Trp
    210                 215                 220

Asp Thr Pro His Leu Phe Ala Asp Phe Val Arg Asn Glu Thr Thr Pro
225                 230                 235                 240

Glu Ser Leu Gly Pro Gln Leu Asn Glu Leu Phe Ser Val Leu Asn Thr
                245                 250                 255

Ala Pro Glu Lys Arg Pro Lys Arg Leu Pro Ser Thr Leu Ala Lys Phe
            260                 265                 270

Pro Tyr Val Asn Gly Ala Leu Phe Ala Glu Pro Leu Ala Ser Glu Tyr
        275                 280                 285

Phe Asp Tyr Gln Met Arg Glu Ala Leu Leu Ala Ala Cys Asp Phe Asp
    290                 295                 300

Trp Ser Thr Ile Asp Val Ser Val Phe Gly Ser Leu Phe Gln Leu Val
305                 310                 315                 320

Lys Ser Lys Glu Ala Arg Arg Ser Asp Gly Glu His Tyr Thr Ser Lys
                325                 330                 335

Ala Asn Ile Met Lys Thr Ile Gly Pro Leu Phe Leu Asp Glu Leu Arg
            340                 345                 350

Ala Glu Ala Asp Lys Leu Val Ser Ser Pro Ser Thr Ser Val Ala Ala
        355                 360                 365

Leu Glu Arg Phe Arg Asp Ser Leu Ser Glu Leu Val Phe Ala Asp Met
    370                 375                 380

Ala Cys Gly Ser Gly Asn Phe Leu Leu Leu Ala Tyr Arg Glu Leu Arg
385                 390                 395                 400

Arg Ile Glu Thr Asp Ile Ile Val Ala Ile Arg Gln Arg Arg Gly Glu
                405                 410                 415

Thr Gly Met Ser Leu Asn Ile Glu Trp Glu Gln Lys Leu Ser Ile Gly
            420                 425                 430

Gln Phe Tyr Gly Ile Glu Leu Asn Trp Trp Pro Ala Lys Ile Ala Glu
        435                 440                 445

Thr Ala Met Phe Leu Val Asp His Gln Ala Asn Lys Glu Leu Ala Asn
    450                 455                 460

Ala Val Gly Arg Pro Pro Glu Arg Leu Pro Ile Lys Ile Thr Ala His
465                 470                 475                 480

Ile Val His Gly Asn Ala Leu Gln Leu Asp Trp Ala Asp Ile Leu Ser
                485                 490                 495

Ala Ser Ala Ala Lys Thr Tyr Ile Phe Gly Asn Pro Pro Phe Leu Gly
            500                 505                 510
```

```
His Ala Thr Arg Thr Ala Glu Gln Ala Gln Glu Leu Arg Asp Leu Trp
    515                 520                 525
Gly Thr Lys Asp Ile Ser Arg Leu Asp Tyr Val Thr Gly Trp His Ala
    530                 535                 540
Lys Cys Leu Asp Phe Phe Lys Ser Arg Glu Gly Arg Phe Ala Phe Val
545                 550                 555                 560
Thr Thr Asn Ser Ile Thr Gln Gly Asp Gln Val Pro Arg Leu Phe Gly
                565                 570                 575
Pro Ile Phe Lys Ala Gly Trp Arg Ile Arg Phe Ala His Arg Thr Phe
            580                 585                 590
Ala Trp Asp Ser Glu Ala Pro Gly Lys Ala Ala Val His Cys Val Ile
            595                 600                 605
Val Gly Phe Asp Lys Glu Ser Gln Pro Arg Pro Arg Leu Trp Asp Tyr
    610                 615                 620
Pro Asp Val Lys Gly Glu Pro Val Ser Val Glu Val Gly Gln Ser Ile
625                 630                 635                 640
Asn Ala Tyr Leu Val Asp Gly Pro Asn Val Leu Val Asp Lys Ser Arg
                645                 650                 655
His Pro Ile Ser Ser Glu Ile Ser Pro Ala Thr Phe Gly Asn Met Ala
            660                 665                 670
Arg Asp Gly Gly Asn Leu Leu Val Glu Val Asp Glu Tyr Asp Glu Val
            675                 680                 685
Met Ser Asp Pro Val Ala Ala Lys Tyr Val Arg Pro Phe Arg Gly Ser
    690                 695                 700
Arg Glu Leu Met Asn Gly Leu Asp Arg Trp Cys Leu Trp Leu Val Asp
705                 710                 715                 720
Val Ala Pro Ser Asp Ile Ala Gln Ser Pro Val Leu Lys Lys Arg Leu
                725                 730                 735
Glu Ala Val Lys Ser Phe Arg Ala Asp Ser Lys Ala Ala Ser Thr Arg
            740                 745                 750
Lys Met Ala Glu Thr Pro His Leu Phe Gly Gln Arg Ser Gln Pro Asp
            755                 760                 765
Thr Asp Tyr Leu Cys Leu Pro Lys Val Val Ser Glu Arg Arg Ser Tyr
    770                 775                 780
Phe Thr Val Gln Arg Tyr Pro Ser Asn Val Ile Ala Ser Asp Leu Val
785                 790                 795                 800
Phe His Ala Gln Asp Pro Asp Gly Leu Met Phe Ala Leu Ala Ser Ser
                805                 810                 815
Ser Met Phe Ile Thr Trp Gln Lys Ser Ile Gly Gly Arg Leu Lys Ser
            820                 825                 830
Asp Leu Arg Phe Ala Asn Thr Leu Thr Trp Asn Thr Phe Pro Val Pro
            835                 840                 845
Glu Leu Asp Glu Lys Thr Arg Gln Arg Ile Ile Lys Ala Gly Lys Lys
    850                 855                 860
Val Leu Asp Ala Arg Ala Leu His Pro Glu Arg Ser Leu Ala Glu His
865                 870                 875                 880
Tyr Asn Pro Leu Ala Met Ala Pro Glu Leu Ile Lys Ala His Asp Ala
                885                 890                 895
Leu Asp Arg Glu Val Asp Lys Ala Phe Gly Ala Pro Arg Lys Leu Thr
            900                 905                 910
Thr Val Arg Gln Arg Gln Glu Leu Leu Phe Ala Asn Tyr Glu Lys Leu
            915                 920                 925
Ile Ser His Gln Pro
```

-continued

930

<210> SEQ ID NO 10
<211> LENGTH: 901
<212> TYPE: PRT
<213> ORGANISM: unknown
<220> FEATURE:
<223> OTHER INFORMATION: MmeI amino acid sequence

<400> SEQUENCE: 10

```
Glu Ile Arg Arg Lys Ala Ile Glu Phe Ser Lys Arg Trp Glu Asp Ala
1               5                   10                  15

Ser Asp Glu Asn Ser Gln Ala Lys Pro Phe Leu Ile Asp Phe Phe Glu
            20                  25                  30

Val Phe Gly Ile Thr Asn Lys Arg Val Ala Thr Phe Glu His Ala Val
        35                  40                  45

Lys Lys Phe Ala Lys Ala His Lys Glu Gln Ser Arg Gly Phe Val Asp
    50                  55                  60

Leu Phe Trp Pro Gly Ile Leu Ile Glu Met Lys Ser Arg Gly Lys
65                  70                  75                  80

Asp Leu Asp Lys Ala Tyr Asp Gln Ala Leu Asp Tyr Phe Ser Gly Ile
                85                  90                  95

Ala Glu Arg Asp Leu Pro Arg Tyr Val Leu Val Cys Asp Phe Gln Arg
            100                 105                 110

Phe Arg Leu Thr Asp Leu Ile Thr Lys Glu Ser Val Glu Phe Leu Leu
        115                 120                 125

Lys Asp Leu Tyr Gln Asn Val Arg Ser Phe Gly Phe Ile Ala Gly Tyr
    130                 135                 140

Gln Thr Gln Val Ile Lys Pro Gln Asp Pro Ile Asn Ile Lys Ala Ala
145                 150                 155                 160

Glu Arg Met Gly Lys Leu His Asp Thr Leu Lys Leu Val Gly Tyr Glu
                165                 170                 175

Gly His Ala Leu Glu Leu Tyr Leu Val Arg Leu Leu Phe Cys Leu Phe
            180                 185                 190

Ala Glu Asp Thr Thr Ile Phe Glu Lys Ser Leu Phe Gln Glu Tyr Ile
        195                 200                 205

Glu Thr Lys Thr Leu Glu Asp Gly Ser Asp Leu Ala His His Ile Asn
    210                 215                 220

Thr Leu Phe Tyr Val Leu Asn Thr Pro Glu Gln Lys Arg Leu Lys Asn
225                 230                 235                 240

Leu Asp Glu His Leu Ala Ala Phe Pro Tyr Ile Asn Gly Lys Leu Phe
                245                 250                 255

Glu Glu Pro Leu Pro Pro Ala Gln Phe Asp Lys Ala Met Arg Glu Ala
            260                 265                 270

Leu Leu Asp Leu Cys Ser Leu Asp Trp Ser Arg Ile Ser Pro Ala Ile
        275                 280                 285

Phe Gly Ser Leu Phe Gln Ser Ile Met Asp Ala Lys Lys Arg Arg Asn
    290                 295                 300

Leu Gly Ala His Tyr Thr Ser Glu Ala Asn Ile Leu Lys Leu Ile Lys
305                 310                 315                 320

Pro Leu Phe Leu Asp Glu Leu Trp Val Glu Phe Glu Lys Val Lys Asn
                325                 330                 335

Asn Lys Asn Lys Leu Leu Ala Phe His Lys Lys Leu Arg Gly Leu Thr
            340                 345                 350

Phe Phe Asp Pro Ala Cys Gly Cys Gly Asn Phe Leu Val Ile Thr Tyr
```

```
                355             360             365
Arg Glu Leu Arg Leu Leu Glu Ile Glu Val Leu Arg Gly Leu His Arg
            370             375             380
Gly Gly Gln Gln Val Leu Asp Ile Glu His Leu Ile Gln Ile Asn Val
385             390             395             400
Asp Gln Phe Phe Gly Ile Glu Ile Glu Glu Phe Pro Ala Gln Ile Ala
            405             410             415
Gln Val Ala Leu Trp Leu Thr Asp His Gln Met Asn Met Lys Ile Ser
            420             425             430
Asp Glu Phe Gly Asn Tyr Phe Ala Arg Ile Pro Leu Lys Ser Thr Pro
            435             440             445
His Ile Leu Asn Ala Asn Ala Leu Gln Ile Asp Trp Asn Asp Val Leu
            450             455             460
Glu Ala Lys Lys Cys Cys Phe Ile Leu Gly Asn Pro Pro Phe Val Gly
465             470             475             480
Lys Ser Lys Gln Thr Pro Gly Gln Lys Ala Asp Leu Leu Ser Val Phe
            485             490             495
Gly Asn Leu Lys Ser Ala Ser Asp Leu Asp Leu Val Ala Ala Trp Tyr
            500             505             510
Pro Lys Ala Ala His Tyr Ile Gln Thr Asn Ala Asn Ile Arg Cys Ala
            515             520             525
Phe Val Ser Thr Asn Ser Ile Thr Gln Gly Glu Gln Val Ser Leu Leu
            530             535             540
Trp Pro Leu Leu Leu Ser Leu Gly Ile Lys Ile Asn Phe Ala His Arg
545             550             555             560
Thr Phe Ser Trp Thr Asn Glu Ala Ser Gly Val Ala Ala Val His Cys
                565             570             575
Val Ile Ile Gly Phe Gly Leu Lys Asp Ser Asp Glu Lys Ile Ile Tyr
            580             585             590
Glu Tyr Glu Ser Ile Asn Gly Glu Pro Leu Ala Ile Lys Ala Lys Asn
            595             600             605
Ile Asn Pro Tyr Leu Arg Asp Gly Val Asp Val Ile Ala Cys Lys Arg
            610             615             620
Gln Gln Pro Ile Ser Lys Leu Pro Ser Met Arg Tyr Gly Asn Lys Pro
625             630             635             640
Thr Asp Asp Gly Asn Phe Leu Phe Thr Asp Glu Lys Asn Gln Phe
            645             650             655
Ile Thr Asn Glu Pro Ser Ser Glu Lys Tyr Phe Arg Arg Phe Val Gly
            660             665             670
Gly Asp Glu Phe Ile Asn Asn Thr Ser Arg Trp Cys Leu Trp Leu Asp
            675             680             685
Gly Ala Asp Ile Ser Glu Ile Arg Ala Met Pro Leu Val Leu Ala Arg
            690             695             700
Ile Lys Lys Val Gln Glu Phe Arg Leu Lys Ser Ala Lys Pro Thr
705             710             715             720
Arg Gln Ser Ala Ser Thr Pro Met Lys Phe Phe Tyr Ile Ser Gln Pro
                725             730             735
Asp Thr Asp Tyr Leu Leu Ile Pro Glu Thr Ser Ser Glu Asn Arg Gln
            740             745             750
Phe Ile Pro Ile Gly Phe Val Asp Arg Asn Val Ile Ser Ser Asn Ala
            755             760             765
Thr Tyr His Ile Pro Ser Ala Glu Pro Leu Ile Phe Gly Leu Leu Ser
            770             775             780
```

```
Ser Thr Met His Asn Cys Trp Met Arg Asn Val Gly Gly Arg Leu Glu
785                 790                 795                 800

Ser Arg Tyr Arg Tyr Ser Ala Ser Leu Val Tyr Asn Thr Phe Pro Trp
                805                 810                 815

Ile Gln Pro Asn Glu Lys Gln Ser Lys Ala Ile Glu Glu Ala Ala Phe
                820                 825                 830

Ala Ile Leu Lys Ala Arg Ser Asn Tyr Pro Asn Glu Ser Leu Ala Gly
            835                 840                 845

Leu Tyr Asp Pro Lys Thr Met Pro Ser Glu Leu Leu Lys Ala His Gln
        850                 855                 860

Lys Leu Asp Lys Ala Val Asp Ser Val Tyr Gly Phe Lys Gly Pro Asn
865                 870                 875                 880

Thr Glu Ile Ala Arg Ile Ala Phe Leu Phe Glu Thr Tyr Gln Lys Met
                885                 890                 895

Thr Ser Leu Leu Pro
            900

<210> SEQ ID NO 11
<211> LENGTH: 44
<212> TYPE: DNA
<213> ORGANISM: unknown
<220> FEATURE:
<223> OTHER INFORMATION: CstMI expression primer

<400> SEQUENCE: 11
gttatgcatt taaggaggta acatatggtt atgccccta cgac              44

<210> SEQ ID NO 12
<211> LENGTH: 35
<212> TYPE: DNA
<213> ORGANISM: unknown
<220> FEATURE:
<223> OTHER INFORMATION: CstMI expression primer

<400> SEQUENCE: 12
gttggatcct cgagggcaag acatatcaag ccttc                       35

<210> SEQ ID NO 13
<211> LENGTH: 24
<212> TYPE: DNA
<213> ORGANISM: unknown
<220> FEATURE:
<223> OTHER INFORMATION: primer NEB1233 (New England Biolabs, Inc.)

<400> SEQUENCE: 13
agcggataac aatttcacac agga                                   24

<210> SEQ ID NO 14
<211> LENGTH: 30
<212> TYPE: DNA
<213> ORGANISM: unknown
<220> FEATURE:
<223> OTHER INFORMATION: primer NEB1238 (New England Biolabs, Inc.)

<400> SEQUENCE: 14
cctataaaaa taggcgtatc acgaggccct                             30

<210> SEQ ID NO 15
<211> LENGTH: 30
<212> TYPE: DNA
<213> ORGANISM: unknown
<220> FEATURE:
```

```
<223> OTHER INFORMATION: primer NEB1242 (New England Biolabs, Inc.)

<400> SEQUENCE: 15
aagtgcggcg acgatagtca tgccccgcgc                              30

<210> SEQ ID NO 16
<211> LENGTH: 30
<212> TYPE: DNA
<213> ORGANISM: unknown
<220> FEATURE:
<223> OTHER INFORMATION: primer NEB1247 (New England Biolabs, Inc.)

<400> SEQUENCE: 16
tacttggagc cactatcgac tacgcgatca                              30

<210> SEQ ID NO 17
<211> LENGTH: 24
<212> TYPE: DNA
<213> ORGANISM: unknown
<220> FEATURE:
<223> OTHER INFORMATION: primer NEB1224 (New England Biolabs, Inc.)

<400> SEQUENCE: 17 gccagggtt ttcccagtca cgac                                     24
```

US 7,186,538 B2

TYPE II RESTRICTION ENDONUCLEASE, CSTMI, OBTAINABLE FROM *CORYNEBACTERIUM STRIATUM* M82B AND A PROCESS FOR PRODUCING THE SAME

BACKGROUND OF THE INVENTION

The present invention relates to a novel type II restriction endonuclease, CstMI. CstMI consists of one polypeptide which possesses two related enzymatic functions. CstMI is an endonuclease that recognizes the DNA sequence 5'-AAGGAG-3' and cleaves the phosphodiester bond between the 20th and 21st residues 3' to this recognition sequence on this DNA strand, and between the 18th and 19th residues 5' to the recognition sequence on the complement strand 5'-CTCCTT-3' to produce a 2 base 3' extension (hereinafter referred to as the CstMI restriction endonuclease). CstMI has a second enzymatic activity that recognizes the same DNA sequence, 5'-AAGGAG-3', but modifies this sequence by the addition of a methyl group to prevent cleavage by the CstMI endonuclease. The present invention also relates to the DNA fragment encoding the CstMI enzyme, a vector containing this DNA fragment, a transformed host containing this DNA fragment, and a process for producing CstMI restriction endonuclease from such a transformed host. CstMI was identified as a potential endonuclease because of its amino acid sequence similarity to MmeI (see U.S. Application Publication No. US-2004-009 191 1-A1, filed concurrently herewith).

Restriction endonucleases are a class of enzymes that occur naturally in prokaryotes. There are several classes of restriction systems known, of which the type II endonucleases are the class useful in genetic engineering. When these type II endonucleases are purified away from other contaminating prokarial components, they can be used in the laboratory to break DNA molecules into precise fragments. This property enables DNA molecules to be uniquely identified and to be fractionated into their constituent genes. Restriction endonucleases have proved to be indispensable tools in modern genetic research. They are the biochemical 'scissors' by means of which genetic engineering and analysis is performed.

Restriction endonucleases act by recognizing and binding to particular sequences of nucleotides (the 'recognition sequence') along the DNA molecule. Once bound, the type II endonucleases cleave the molecule within, or to one side of, the sequence. Different restriction endonucleases have affinity for different recognition sequences. The majority of restriction endonucleases recognize sequences of 4 to 6 nucleotides in length, although recently a small number of restriction endonucleases which recognize 7 or 8 uniquely specified nucleotides have been isolated. Most recognition sequences contain a dyad axis of symmetry and in most cases all the nucleotides are uniquely specified. However, some restriction endonucleases have degenerate or relaxed specificities in that they recognize multiple bases at one or more positions in their recognition sequence, and some restriction endonucleases recognize asymmetric sequences. HaeIII, which recognizes the sequence 5'-GGCC-3', is an example of a restriction endonuclease having a symmetrical, non-degenerate recognition sequence; HaeII, which recognizes 5'-(Pu)GCGC(Py)-3' typifies restriction endonucleases having a degenerate or relaxed recognition sequence; while BspMI, which recognizes 5'-ACCTGC-3' typifies restriction endonucleases having an asymmetric recognition sequence. Type II endonucleases with symmetrical recognition sequences generally cleave symmetrically within or adjacent to the recognition site, while those that recognize asymmetric sequences tend to cleave at a distance of from 1 to 20 nucleotides to one side of the recognition site. The enzyme of this application, CstMI, (along with MmeI) has the distinction of cleaving the DNA at the farthest distance from the recognition sequence of any known type II restriction endonuclease. More than two hundred unique restriction endonucleases have been identified among several thousands of bacterial species that have been examined to date.

A second component of restriction systems are the modification methylases. These enzymes are complementary to restriction endonucleases and they provide the means by which bacteria are able to protect their own DNA and distinguish it from foreign, infecting DNA. Modification methylases recognize and bind to the same nucleotide recognition sequence as the corresponding restriction endonuclease, but instead of breaking the DNA, they chemically modify one or other of the nucleotides within the sequence by the addition of a methyl group. Following methylation, the recognition sequence is no longer cleaved by the restriction endonuclease. The DNA of a bacterial cell is modified by virtue of the activity of its modification methylase and it is therefore insensitive to the presence of the endogenous restriction endonuclease. It is only unmodified, and therefore identifiably foreign, DNA that is sensitive to restriction endonuclease recognition and cleavage. Modification methyltransferases are usually separate enzymes from their cognate endonuclease partners. In some cases, there is a single polypeptide that possesses both a modification methyltransferase function and an endonuclease function, for example, Eco57I. In such cases, there is usually a second methyltransferase present as part of the restriction-modification system. CstMI, however, consists of a single polypeptide that possesses both a modification methyltransferase function and an endonuclease function but does not have a second methyltransferase peptide as part of the restriction modification system. In this regard CstMI is similar to the MmeI restriction modification system.

Endonucleases are named according to the bacteria from which they are derived. Thus, the species *Haemophilus aegyptius*, for example synthesizes 3 different restriction endonucleases, named HaeI, HaeII and HaeIII. These enzymes recognize and cleave the sequences 5'-(W)GGCC (W)-3',5'-(Pu)GCGC(Py)-3' and 5'-GGCC-3' respectively. *Escherichia coli* RY13, on the other hand, synthesizes only one enzyme, EcoRI, which recognizes the sequence 5'-GAATTC-3'.

While not wishing to be bound by theory, it is thought that in nature, restriction endonucleases play a protective role in the welfare of the bacterial cell. They enable bacteria to resist infection by foreign DNA molecules such as viruses and plasmids that would otherwise destroy or parasitize them. They impart resistance by binding to infecting DNA molecules and cleaving them in each place that the recognition sequence occurs. The disintegration that results inactivates many of the infecting genes and renders the DNA susceptible to further degradation by exonucleases.

More than 3000 restriction endonucleases have been isolated from various bacterial strains. Of these, more than 240 recognize unique sequences, while the rest share common recognition specificities. Restriction endonucleases which recognize the same nucleotide sequence are termed "isoschizomers." Although the recognition sequences of isoschizomers are the same, they may vary with respect to site of cleavage (e.g., XmaI v. SmaI, Endow, et al., *J. Mol. Biol.* 112:521 (1977); Waalwijk, et al., *Nucleic Acids Res.*

5:3231 (1978)) and in cleavage rate at various sites (XhoI v. PaeR7I, Gingeras, et al., *Proc. Natl. Acad. Sci. U.S.A.* 80:402 (1983)).

Restriction endonucleases have traditionally been classified into three major classes; type I, type II and type III. The type I restriction systems assemble a multi-peptide complex consisting of restriction polypeptide, modification polypeptide, and specificity, or DNA recognition, polypeptide. Type I systems require a divalent cation, ATP and S-adenosylmethionine (SAM) as cofactors. Type I systems cleave DNA at random locations up to several thousand basepairs away from their specific recognition site. The type III systems generally recognize an asymmetric DNA sequence and cleave at a specific position 20 to 30 basepairs to one side of the recognition sequence. Such systems require the cofactor ATP in addition to SAM and a divalent cation. The type III systems assemble a complex of endonuclease polypeptide and modification polypeptide that either modifies the DNA at the recognition sequence or cleaves. Type III systems produce partial digestion of the DNA substrate due to this competition between their modification and cleavage activities, and so have not been useful for genetic manipulation.

CstMI can be classified as a type II endonuclease in that it does not require ATP for DNA cleavage activity. Unlike other type II enzymes, however, CstMI consists of a single polypeptide that combines both endonuclease and modification activities and is sufficient by itself to form the entire restriction modification system. CstMI, like the related endonuclease MmeI, cleaves the farthest distance from the specific DNA recognition sequence of any type II endonuclease. CstMI is quite large and appears to have three functional domains combined in one polypeptide. These consist of an amino-terminal DNA cleavage domain which may also be involved in DNA recognition, a DNA modification domain most similar to the gamma-class N6 mA methyltransferases, and a carboxy-terminal domain presumed to be involved in dimer formation and possibly DNA recognition. The enzyme requires SAM for both cleavage and modification activity. The single CstMI polypeptide is sufficient to modify the plasmid vector carrying the gene in vivo to provide protection against CstMI cleavage in vitro, yet it is also able to cleave unmodified DNAs in vitro when using the endonuclease buffer containing Mg++ and SAM.

There is a continuing need for novel type II restriction endonucleases. Although type II restriction endonucleases which recognize a number of specific nucleotide sequences are currently available, new restriction endonucleases which recognize novel sequences provide greater opportunities and ability for genetic manipulation. Each new unique endonuclease enables scientists to precisely cleave DNA at new positions within the DNA molecule, with all the opportunities this offers.

SUMMARY OF THE INVENTION

In accordance with the present invention, there is provided a novel DNA fragment encoding a novel restriction endonuclease, obtainable from *Corynebacterium striatum* M82B (GenBank Accession #AAG03371) or from the transformed *E. coli* strain NEB#1530. The endonuclease is hereinafter referred to as "CstMI", which endonuclease:

(1) recognizes the nucleotide sequence 5'-AAGGAG-3' in a double-stranded DNA molecule as shown below,

```
5'-AAGGAG-3'
```

```
-continued
3'-TTCCTC-5'
```

(wherein G represents guanine, C represents cytosine, A represents adenine and T represents thymine;

(2) cleaves DNA in the phosphodiester bond following the 20th nucleotide 3' to the recognition sequence 5'-AAG-GAG-3 and preceding the 18th nucleotide 5' to the recognition sequence in the complement strand of 5'-CTCCTT-3' to produce a 2 base 3' extension:

```
5'-AAGGAG(N20)/-3'

3'-TTCCTC(N18)/-5'; and
```

(3) methylates the recognition sequence specified in (1) in vivo to protect the host DNA from cleavage by the CstMI endonuclease activity;

The present invention further relates to a process for the production of the restriction endonuclease CstMI. This process comprises culturing a transformed host, such as *E. coli*, containing the DNA fragment encoding the CstMI restriction system polypeptide, collecting the cultured cells, obtaining a cell-free extract therefrom and separating and collecting the restriction endonuclease CstMI from the cell-free extract.

BRIEF DESCRIPTION OF THE FIGURES

FIG. 1—Agarose gel showing CstMI cleavage of lambda, T7, phiX174, pBR322 and pUC19 DNAS. Lanes 1, 7, 13 and 20: lambda-HindIII, PhiX174-HaeIII size standards; lane 2: pUC19 DNA+CstMI+Eco0109I; lane 3: pUC19 DNA+CstMI+PstI; lane 4: pUC19 DNA+CstMI+AlwNI; lane 5: pUC19 DNA+CstMI+XmnI; lane 6: pUC19 DNA+CstMI; lane 8: pBR322 DNA=CstMI+ClaI; lane 9: pBR322 DNA+CstMI+NruI; lane 10: pBR322 DNA+CstMI+NdeI; lane 11, pBR322 DNA+CstMI+PstI; lane 12: pBR322 DNA+CstMI; lane 14: PhiX174 DNA=CstMI+PstI; lane 15: PhiX174 DNA+CstMI+SspI; lane 16: PhiX174 DNA+CstMI+NciI; lane 17: PhiX174 DNA+CstMI+StuI; and lane 18: PhiX174 DNA+CstMI FIG. 2—DNA sequence of the CstMI gene locus (SEQ ID NO:1).

FIG. 3—Amino acid sequence of the CstMI gene locus (SEQ ID NO:2).

FIG. 4—Agarose gel showing CstMI protection of pTBCstMI.3 DNA and cleavage of unmodified DNA substrate. lane 1 and 5: lambda-HindIII, PhiX174-HaeIII size standards; lane 2: pTBCstMI.3+Eco0109I; lane 3: pTBCstMI.3+eco0109I+CstMI; lane 4: pTBCstMI.3+CstMI+pUC19 DNA.

FIG. 5—Determination of the CstMI cleavage site.

FIG. 5A: Location of cleavage on 5'AAGGAG-3" strand (SEQ ID NO:3, SEQ ID NO:4 and SEQ ID NO:5).

FIG. 5B: location of cleavage on 5-CTCCTT-3' strand (SEQ ID NO:6, SEQ ID NO:7 and SEQ ID NO:8).

FIG. 6—Sequence alignment of CstMI (SEQ ID NO:9) and MmeI (SEQ ID NO:10) amino acid sequences FIG. 7—Photograph depicting titer of CstMI crude extract on lambda DNA. The reaction mixture is NEBuffer 4 supplmented with 100 uM SAM with 1 Ug lambda DNA per 50 uL. Digestion took place at 37° C. for one hour. Lane 1—lambda-HindIII and PhiX174—HaeIII marker; Lane 2-8 uL crude extract/50 uL reaction mix; Lane 3-4 uL crude extract/50 uL reaction mix; Lane 4-2 uL crude extract/50 uL reaction mix; Lane 5-1 uL crude extract/50 uL reaction mix; Lane 6-0.5 uL crude extract/50 uL reaction mix; Lane 7-0.25 uL crude extract/50 uL reaction mix.

DETAILED DESCRIPTION OF THE INVENTION

Figure 7:
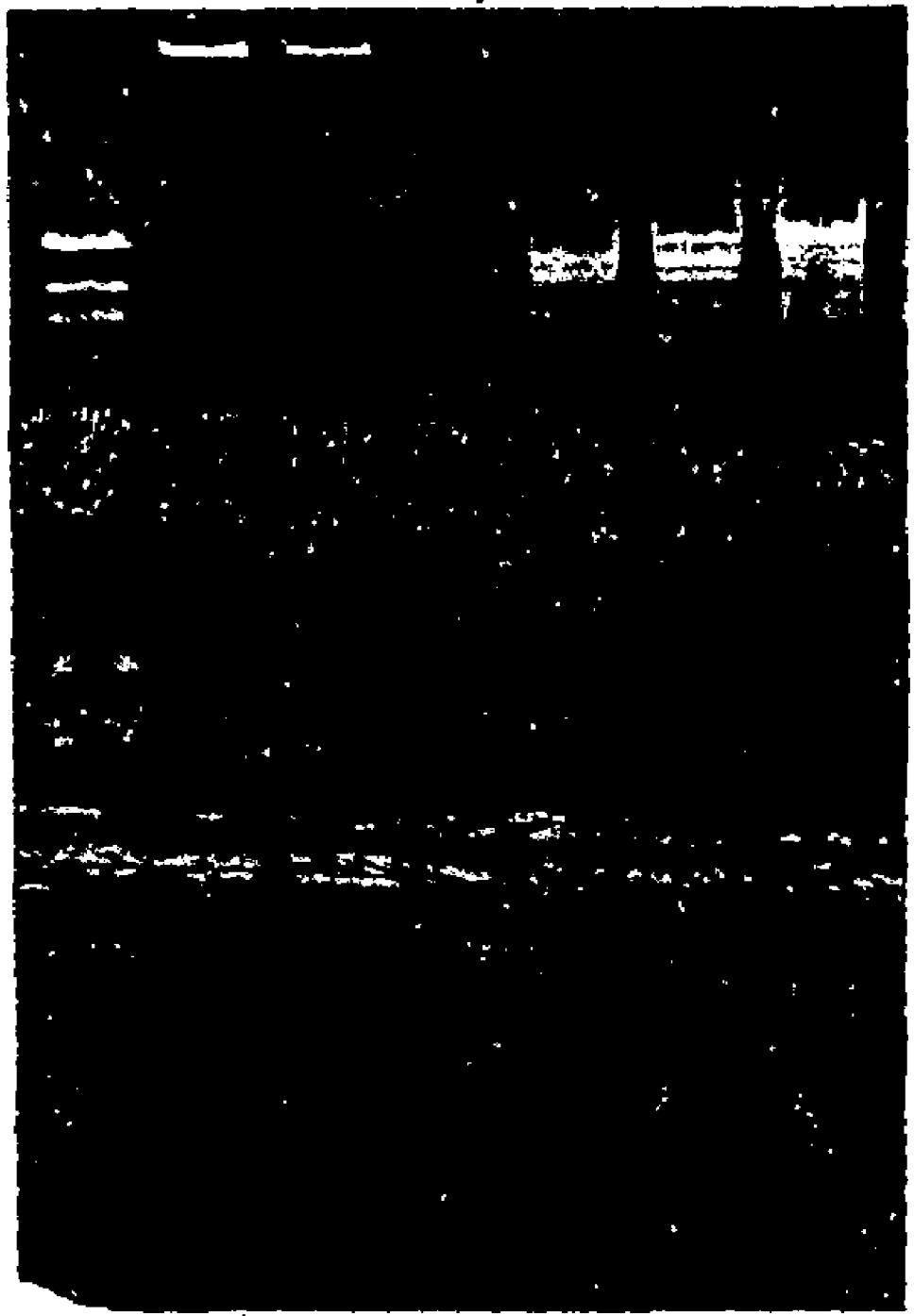

The MmeI endonuclease was cloned New England Biolabs, Inc. (Beverly, Mass.) and its amino acid sequence was determined (U.S. Application Publication No. US-2004-0091911-A1, filed concurrently herewith, the disclosure of which is herein incorporated by reference). A BLAST search of the Genbank database using the MmeI endonuclease amino acid sequence as the query returned a number of sequences that were highly significantly similar to MmeI. Among these was a sequence, GenBank accession #AAG03371, which encoded a gene labeled gcrY, and annotated as a "hypothetical 107.5 kDa protein". This hypothetical protein was encoded on a 51,409 base pair plasmid isolated from *Corynebacterium striatum* M82B (see Tauch, A., Krieft,S., Kalinowski,J. and Puhler,A., "The 51,409-bp R-plasmid pTP1O from the multiresistant clinical isolate *Corynebacterium striatum* M82B is composed of DNA segments initially identified in soil bacteria and in plant, animal, and human pathogens" Mol. Gen. Genet. 263 (1), 1–11 (2000)). A sample of this plasmid DNA was kindly provided by the author, Andreas Tauch. The DNA sequence encoding and flanking the potential endonuclease gene was known. Primers were designed to specifically amplify the gene from *Corynebacterium striatum* M82B DNA, with convenient restriction enzyme sites added to facilitate cloning into a vector. The amplified gene was inserted into an expression vector and cloned into an *E. coil* host. Transformed host cells were tested and several were found to express an endonuclease activity when incubated in NEB-uffer 4 supplemented with 100 mM SAM (S-adenosyl-methionine) (FIG. 7). The DNA recognition sequence of this new endonuclease was determined by mapping the positions of cleavage in pUC 19, pBR 322 and PhiXl 74 DNAs. These locations of cleavage were found to be consistent with the sequence 5'-AAGGAG-3'(or 5'-CTCCTT-3' on the complement DNA strand). This novel enzyme was named CstMI (from *Corynebacterium striatum* M82B). This recognition sequence is quite different from that of MmeI, which recognizes 5'-TCC(Pu)AC-3', even though the enzymes share approximately 40% a identical and 51% a similar amino acids in their sequences (FIG. 6). The point of DNA cleavage relative to the recognition sequence was determined by cutting an appropriate DNA with CstMI, purifying the DNA and subjecting it to standard dideoxy automated sequencing. CstMI was found to cleave DNA at the same position relative to its recognition sequence as MmeI; namely after the 20th nucleotide 3' to the 5'-AAGGAG-3' recognition sequence strand, and before the 18th nucleotide 5' to the 5'-CTCCTT-3' recognition sequence strand, producing a 2 base pair 3' extension. CstMI was also found to in vivo modify the recombinant expression vector, pTBCstMI.3, such that it was protected against CstMI endonuclease activity in vitro.

In Example I below we describe the cloning and expression of CstMI.

In Example II we obtained CstMI by culturing a transformed host carrying the CstMI gene, such as *E. coli* ER2683 carrying pTBCstMI.3 and recovering the endonuclease from the cells. A sample of *E. coli* ER2683 carrying pTBCstMI.3 (NEB#1530) has been deposited under the terms and conditions of the Budapest Treaty with the American Type Culture Collection (ATCC) on Jun. 25, 2003 and bears the ATCC Accession No. PTA-5291.

For recovering the enzyme of the present invention *E. coli* carrying pTBCstMI.3 (NEB#1530) may be grown using any suitable technique. For example, *E. coli* carrying pTBCstMI.3 may be grown in Luria broth media containing 100 μg/ml ampicillin and incubated aerobically at 37° C. with aeration. Cells in the late logarithmic stage of growth are induced by adding 0.3 mM IPTG, grown for an additional 4 hours, collected by centrifugation and either disrupted immediately or stored frozen at −70° C.

The CstMI enzyme can be isolated from *E. coli* carrying pTBCstMI.3 cells by conventional protein purification techniques. For example, cell paste is suspended in a buffer solution and treated by sonication, high pressure dispersion or enzymatic digestion to allow extraction of the endonuclease by the buffer solution. Intact cells and cellular debris are then removed by centrifugation to produce a cell-free extract containing CstMI. The CstMI endonuclease, along with its corresponding intrinsic methylase activity, is then purified from the cell-free extract by ion-exchange chromatography, affinity chromatography, molecular sieve chromatography, or a combination of these methods to produce the endonuclease of the present invention.

The present invention is further illustrated by the following Examples. These Examples are provided to aid in the understanding of the invention and are not construed as a limitation thereof.

The references cited above and below are herein incorporated by reference.

EXAMPLE I

Cloning the CstMI Endonuclease

1. Identifying the CstMI endonuclease gene from *Corynebacterium straitum* M82B 51,409 bp plasmid pTP10 DNA: The putative CstMI endonuclease open reading frame was identified by a BLAST search of the nonredundant sequences in the GenBank database. The BLAST algorithm was performed using the MmeI amino acid sequence as the query, with parameters of word size=3, matrix=BLOSUM62, gap costs of 11 for the existence of a gap and 1 for an extension of a gap, with no masking for low complexity. The open reading for the CstMI endonuclease, found in the *Corynebacterium straitum* M82B 51,409 bp plasmid pTP10 DNA, labeled gcrY and annotated as a 'hypothetical protein," yielded a very highly significant expectation value of $E=e^{-171}$, making it an excellent candidate for a new MmeI-like endonuclease.

2. DNA purification: A DNA preparation of the *Corynebacterium straitum* M82B 51,409 bp plasmid pTP10 was kindly supplied by Andreas Tauch.

3. Cloning the CstMI open reading frame: Oligonucleotide primers were synthesized to specifically amplify the CstMI gene from *Corynebacterium striatum* pTP10 plasmid DNA for expression in the cloning vector pRRS (Skoglund, Gene 88:1–5 (1990)). The forward primer contained a NsiI site for cloning, a stop codon in frame with the lacZ gene of the vector, a consensus *E. coli* ribosome binding site, the ATG start codon for translation and 20 nucleotides that matched the *Corynebacterium striatum* pTP10 plasmid DNA sequence at the beginning of the CstMI open reading frame:

```
CstMI expression primer forward (#282-48):
5' - GTTATGCATTTAAGGAGGTAACATATGGTTATGGCCCCTACGAC-3'  (SEQ ID NO: 11)
```

The reverse primer contained a BamHI for cloning and 21 nucleotides that matched the the *Corynebacterium striatum* DNA sequence beginning at the C base in the complement strand corresponding to the G base of the stop codon TAG of the CstMI open reading frame:

```
CstMI expression primer reverse (#282-49):
5' -GTTGGATCCTCGAGGGCAAGACATATCAAGCCTTC -3'  (SEQ ID NO: 12)
```

The CstMI gene was amplified in a PCR reaction by combining:
50 µl 10× Thermopol buffer (NEB)
30 µl 4 mM DNTP solution
12.5 µl forward primer #282-48 (10 µM stock)
12.5 µl reverse primer #282-49 (10 µM stock)
5 µl *Corynebacterium striatum* pTP10 plasmid DNA (5 µg/ml stock)
387 µl dH$_2$O
3 µl (6 units) Vent® DNA polymerase The reaction was mixed and aliquoted into 5 tubes of 80 µl each. MgSO$_4$ was added (100 mM stock) to bring the final concentration of Mg++ ions to 2 mM, 3 mM, 4 mM, 5 nM and 6 mM respectively. The cycling parameters were 95° C. for 30 seconds, 58° C. for 30 seconds, 72° C. for 3 minutes, for 5 cycles, followed by 23 cycles of 95° C. for 30 seconds, 64° C. for 30 seconds, 72° C. for 3 minutes. The reactions were analyzed by gel electrophoresis and the 2 mM through 5 mM Mg++ reactions were found to contain a DNA band of the desired size of 2.9 kb. These reactions were pooled and the 2.9 kb band was gel purified. The 2.9 kb amplified CstMI gene fragment was digested with BamHI and NsiI endonucleases (NEB) in the following reaction conditions:
2 µl 10× BamHI reaction buffer (NEB)
8 µl CstMI gene 2.9 kb amplified DNA fragment
10 µl dH2O
0.5 µl BamHI endonuclease (10 units)
0.5 µl PstI endonuclease (10 units)

The reaction was mixed and incubated for 1 hour at 37° C. The endonucleases were heat killed by incubating at 80° C. for 20 minutes.

The cleaved CstMI gene DNA fragment was ligated to the pRRS vector. 10 µl of the digested, purified 2.9 kb CstMI fragment was combined with 3 µl pRRS vector previously cleaved with BamHI and PstI and purified, 5 µl dH$_2$O, 2 µl 10×T4 DNA Ligase Buffer (NEB), the reaction was mixed, and 1 µl of T4 DNA Ligase was added. The reaction was incubated at 16° C. for 16 hours. 5 µl of the ligation reaction was transformed into 100 µl electro-competent *E. coli* ER2683 cells, the cells were grown out in 1 ml Luria broth for 45 minutes, then 20 µl and 200 µl were plated on L-broth plates containing 100 µg/ml ampicillin and incubated at 37° C. overnight. Approximately 100 transformants were obtained and 4 representatives were analyzed as follows: plasmid from each colony was isolated by miniprep procedures and digested with PvuII endonucleases to determine if they contained the correct size insert. 3 of the 4 transformants had the correct size insert of approximately 2900 bp. The 3 insert containing clones were digested with MmeI endonuclease to see if this open reading frame produced an enzyme that recognized the same sequence as MmeI and thus protected the plasmid DNA of the clone from MmeI digestion. All three clones were cut with MmeI endonuclease, indicating that this enzyme did not modify the DNA at the MmeI recognition site.

Two of the clones were tested to see if they produced any endonuclease activity. The purified plasmid DNAs were transformed into *E. coli* strain ER2796. 6 colonies that grew up from one of the clones were tested for endonuclease activity. The six colonies were inoculated into 50 ml luria broth containing 100' g/ml ampicillin and grown overnight at 37° C. with shaking. The cells were then harvested by centrifugation, resuspended in 1.5 ml buffer (20 mM Tris-HCl, 1 mM DTT, 0.1 mM EDTA) and lysed by sonication. The lysate was assayed for endonuclease activity by serial dilution of the lysate in 1× reaction buffer NEBuffer 4 (New England Biolabs) containing 20 µg/ml lambda DNA substrate and supplemented with SAM at 80 µM final concentration. The reactions were incubated for 1 hour at 37° C. The reaction products were analyzed by agarose gel electrophoresis on a 1% agarose gel in 1×TBE buffer. Two of the six clones clearly had endonuclease activity, three did not show endonuclease activity and one appeared to be a contaminant (not an *E. coli* clone). The most active clone was designated strain NEB#1530 and was used for subsequent production of CstMI. The plasmid construct expressing CstMI activity in this clone was designated pTBCstMI.3.

EXAMPLE II

Production of CstMI Endonuclease

A single colony of *E. coli* ER2683 carrying the CstMI gene in the vector pTBCstMI.3 (NEB#1530) was grown in 2 liter of Luria broth. The cells were grown aerobically at 37° C. for 14 hours, then IPTG was added to 0.3 mM final concentration and the cells were grown for 2 more hours. The cells were collected by centrifugation, yielding two grams of wet cell pellet.

4 grams of CstMI expressing NEB#1530 cell pellet was suspended in 10 milliliters of Buffer A (20 mM Tris-HCl (pH 8.0), 50 mM NaCl, 1.0 mM DTT, 0.1 mM EDTA) and sonicated for 6 minutes at a 50% pulse to disrupt the cells. The lysate was centrifuged at ~30,000×G for 15 minutes and the supernatant collected. (FIG. 7) The supernatant solution was applied to a 8 ml Heparin Hyper-D column (BioSepra SA) which had been equilibrated in buffer A. A 16 mL wash of buffer A was applied, then a 150 mL gradient from 0.05M to 1M NaCl in buffer A was applied and 3 mL fractions were collected. Fractions were assayed for CstMI endonuclease activity by incubating with 1 µg Lambda DNA (NEB) in 50 µl NEBuffer 4, supplemented with 100 µM S-adenosyl-L-methionine (SAM) for 15 minutes at 37° C. CstMI activity eluted at 0.33M to 0.44M NaCl.

The Heparin Hyper-D column fractions containing the CstMI activity were pooled, diluted to 50 mM NaCl with buffer A (without NaCl) and applied to a 3 ml Heparin-TSK column (TosoHaas) which had been equilibrated with buffer A. A wash of 6 ml buffer A was applied, followed by a 50 ml linear gradient of NaCl from 0.05M to 11.0M in buffer A. Fractions were collected and assayed from CstMI endonuclease activity. The CstMI activity eluted between 0.44 M and 0.48 M NaCl.

The Heparin-TSK column fractions containing CstMI activity were pooled, diluted to 50 mM NaCl with buffer A (without NaCl) and applied to a 1 ml Mono-Q FPLC column (Pharmacia) equilibrated with buffer A. A wash of 2 ml buffer A was applied, followed by a 40 ml linear gradient of NaCl from 0.05 M to 0.6 M in buffer A. 1 ml fractions were collected and assayed from CstMI endonuclease activity. CstMI eluted from 0.28 M to 0.4 M NaCl. The purified CstMI fractions were pooled (4 ml) and dialyzed against storage buffer (10 mM Tris (pH 7.9), 50 mM KCl, 1 mM DTT, 0.1 mM EDTA, 50% glycerol). The purified CstMI enzyme was stored at −20° C. The CstMI endonuclease obtained was substantially pure.

Activity Determination

Samples from 1–4 µl were added to 50 µl substrate solution consisting of 1× NEBuffer 4, 100 µM S-adenosyl-L-methionine, and 1 µg DNA (lambda, PhiX174, pBR322 or pUC19 DNAs). Reactions were incubated for 15 minutes at 370, received 20 µl stop solution and were analyzed by electrophoresis on a 1% agarose gel (FIG. 1)

EXAMPLE III

Determination of the CstMI Endonuclease Cleavage Site

The location of CstMI cleavage relative to the recognition sequence was determined by cleaving a suitable DNA molecule and then performing DNA sequencing from a suitable primer to the end of the cleaved DNA template. In this example pUC19 DNA and pBR322 DNA were employed as the template. These templates were chosen because there were CstMI sites in both orientations located within several hundred base pairs from standard sequencing primers. Any sequenceable DNA that has a CstMI site within several hundred base pairs of a priming site will work for this analysis, however. The pUC19 DNA was cleaved with CstMI by combining:

50 µl 10× NEBuffer #4
15 µl pUC19 DNA (15 µg)
435 µl dH$_2$O
20 µl CstMI (fraction 28 off the MonoQ column)

and incubating for 15 minutes at 37° C. pBR322 DNA and pUC19-Adeno2 BC4 DNAs were cut using the same conditions. The cleaved DNAs were purified and concentrated using a Qiagen QiaPrep DNA spin column according to the manufacturer's instructions. The DNAs were eluted in a volume of 100 µl.

Sequencing Reactions

The sequencing reactions were performed using an ABI377 DNA sequencer according to the manufacturer's instructions. The cleaved pUC19 DNA was sequenced with primers NEB1233 and NEB1238 (New England Biolabs) to examine the cut at position 240:

```
NEB1233 5'-AGCGGATAACAATTTCACACAGGA-3'      (SEQ ID NO: 13)

NEB1238 5'-CCTATAAAAATAGGCGTATCACGAGGCCCT-3 (SEQ ID NO: 14)
```

The cleaved pBR322 DNA was sequenced with primers NEB1242 and NEB1247 (New England Biolabs) to examine the cut at 537.

```
NEB1242: 5'-AAGTGCGGCGACGATAGTCATGCCCCGCGC-3'  (SEQ ID NO: 15)

NEB1247: 5'-TACTTGGAGCCACTATCGACTACGCGATCA-3'  (SEQ ID NO: 16)
```

A pUC19-derived plasmid (pUC19-Adeno2 BC4) that contains a fragment of Adeno2 DNA from BstBI (10,670) to ClaI (18,657) inserted at the AccI site of pUC19 was also cut with CstMI and sequenced with primer NEB1224 to examine the CstMI site of Adeno2 DNA at 10,743.

```
NEB1224:
5' -CGCCAGGGTTTTCCCAGTCACGAC-3'    (SEQ ID NO: 17)
```

The results indicate CstMI cleaves DNA between the 20th and the 21th nucleotides 3' to the recognition sequence 5'-AAGGAG-3 in this DNA strand, and between the 18th and 19th nucleotides 5' to the recognition sequence in the complement stand, 5'-CTCCTT-3', to produce a 2 base 3' extension (FIG. 5).

EXAMPLE IV

The CstMI Endonuclease Provides In Vivo Protection Against CstMI Cleavage

The plasmid pTBCstMI.3 was purified from NEB#1530 using the Qiagen miniprep protocol. This plasmid has two CstMI sites in the vector backbone, and two site within the CstMI gene. The plasmid was digested with CstMI to test whether this DNA was resistant to CstMI endonuclease activity, which would indicate that the single CstMI gene was able to methylate DNA in vivo to protect the host DNA against its endonuclease activity. To test this the following were combined:

6 µl pTBCstMI.3 plasmid DNA
15 µl 10× NEBuffer 4
0.5 µl SAM (32 mM stock solution)
129 µl dH2O
3 µl Eco0109I endonuclease (to linearize the plasmid)

The reaction mix was split into two pools, one of 50 µl, to which nothing more was added, and one of 100 µl, to which CstMI endonuclease was added. The CstMI containing reaction was then split into two equal portions and 0.5 µl of pUC19 DNA (0.5 µg) was added to one half as a positive control for CstMI endonuclease activity (FIG. 4).

What is claimed is:

1. Isolated DNA coding consisting of the DNA for the CstMI restriction enzyme, wherein the isolated DNA is obtainable from *Corynebacteriurn striatum*.

2. A recombinant DNA vector comprising the DNA of claim 1.

3. Isolated DNA coding consisting of the DNA for the CstMI endonuclease/methyltransferase, wherein the isolated DNA is obtainable from ATCC Accession No. PTA-5291.

4. A vector which comprises the isolated DNA of claim 3.

5. A host cell transformed by the vector of claim 2 or 4.

6. A method of producing an CstMI restriction endonuclease and CstMI methylase comprising culturing a host cell transformed by a vector comprising isolated DNA consisting of the DNA coding for CstMI endonuclease and methyltransferase under conditions suitable for expression of said endonuclease.

* * * * *

UNITED STATES PATENT AND TRADEMARK OFFICE
CERTIFICATE OF CORRECTION

PATENT NO. : 7,186,538 B2
APPLICATION NO. : 10/616689
DATED : March 6, 2007
INVENTOR(S) : Richard D. Morgan et al.

Page 1 of 1

It is certified that error appears in the above-identified patent and that said Letters Patent is hereby corrected as shown below:

In the Specification:

On Face page, in column 2, under "ABSTRACT", before "5'-CTCCTT-3'" delete "stand," and insert -- strand --, therefor.

At column 6, line number 39, delete "*straitum*" and insert -- *striatum* --, therefor.

At column 6, line number 55, delete "*straitum*" and insert -- *striatum* --, therefor.

At column 10, line number 40, delete "stand" and insert -- strand --, therefor.

At column 10, line number 50, delete "site" and insert -- sites --, therefor.

At column 7, line number 29, delete "nM" and insert -- mM --, therefor.

At column 8, line number 22, delete "100' g/ml" and insert -- 100 µg/ml --, therefor.

At column 9, line number 4, delete "11.0M" and insert -- 1.0M --, therefor.

At column 9, line number 39, delete "370" and insert -- 37° --, therefor.

At column 31, claim number 1, line number 32, delete "Corynebacteriurn" and insert -- Corynebacterium --, therefor.

Signed and Sealed this
Tenth Day of May, 2011

David J. Kappos
*Director of the United States Patent and Trademark Office*